United States Patent
Alsulaimani et al.

(10) Patent No.: US 10,080,626 B1
(45) Date of Patent: Sep. 25, 2018

(54) INTEGRAL RESTORATION MATRIX SYSTEM

(71) Applicant: KING SAUD UNIVERSITY, Riyadh (SA)

(72) Inventors: Reem Siraj Alsulaimani, Riyadh (SA); Sara Nasser Aldosary, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/828,124

(22) Filed: Nov. 30, 2017

(51) Int. Cl.
*A61C 5/82* (2017.01)
*A61C 5/85* (2017.01)
*A61C 5/88* (2017.01)
*A61C 3/06* (2006.01)

(52) U.S. Cl.
CPC ............ *A61C 5/85* (2017.02); *A61C 5/82* (2017.02); *A61C 5/88* (2017.02); *A61C 3/06* (2013.01)

(58) Field of Classification Search
CPC .... A61C 5/85; A61C 5/88; A61C 5/82; A61C 3/06
See application file for complete search history.

(56) References Cited

U.S. PATENT DOCUMENTS

| | | | |
|---|---|---|---|
| 4,704,087 A | 11/1987 | Dragan | |
| 5,382,160 A | 1/1995 | Shemet | |
| 6,375,463 B1 * | 4/2002 | McLean | A61C 5/85 |
| | | | 433/149 |
| 6,439,886 B1 | 8/2002 | Thoreson | |
| 6,712,608 B2 | 3/2004 | Bills | |
| 7,083,412 B1 * | 8/2006 | Karapetyan | A61C 5/85 |
| | | | 433/148 |
| 8,070,490 B1 * | 12/2011 | Roetzer | A61C 5/85 |
| | | | 433/142 |
| 8,272,869 B2 | 9/2012 | Galler | |
| 9,192,452 B2 | 11/2015 | Fatiny | |
| 2004/0146838 A1 * | 7/2004 | Nugiel | A61C 5/00 |
| | | | 433/226 |
| 2006/0275734 A1 * | 12/2006 | Vallittu | A61K 6/0032 |
| | | | 433/39 |
| 2009/0042161 A1 * | 2/2009 | Jodaikin | A61C 19/063 |
| | | | 433/80 |
| 2011/0262878 A1 * | 10/2011 | Galler | A61C 5/85 |
| | | | 433/39 |
| 2014/0038130 A1 | 2/2014 | Pun | |
| 2015/0125810 A1 * | 5/2015 | Jodaikin | A61C 19/063 |
| | | | 433/80 |
| 2015/0150651 A1 * | 6/2015 | McDonald | A61C 5/127 |
| | | | 433/149 |

* cited by examiner

*Primary Examiner* — Nicholas Lucchesi
(74) *Attorney, Agent, or Firm* — Richard C. Litman

(57) ABSTRACT

The integral restoration matrix system includes an arcuate frame having opposed upper and lower arcuate members and first and second opposed side members. The arcuate frame defines an open interior region. A matrix sheet is secured to the arcuate frame and extends across, and covers, the open interior region defined by the arcuate frame. First and second upper arcuate retaining arms are secured to, and extend from, respective upper ends of the first and second opposed side members. First and second lower arcuate retaining arms are secured to, and extend from, respective lower ends of the first and second opposed side members. A hemostatic mesh is secured to the lower arcuate member of the arcuate frame.

13 Claims, 5 Drawing Sheets

INTEGRAL RESTORATION MATRIX SYSTEM

BACKGROUND

1. Field

The disclosure of the present patent application relates to dental restorations, and particularly to a restoration matrix system which combines a matrix band, interproximal wedge and matrix retainer in an integral tool for dental restorations.

2. Description of the Related Art

A dental restoration or dental filling is a treatment to restore the function, integrity, and morphology of missing tooth structure resulting from caries or external trauma. A typical matrix system for dental restoration includes a matrix, or matrix band, as well as a wedge and a matrix retainer. FIG. 2 illustrates a conventional prior art matrix system in use in a restoration of an occlusoproximal cavity (indicated at C in FIG. 2) in a tooth. In FIG. 2, a pair of matrix bands M are shown on either end of the tooth, although it should be understood that often only a single such matrix band M is used, dependent upon the nature of the cavity to be filled. Matrix bands M are placed around the tooth T that is to be worked on. To ensure that the hardened filling, whether of the amalgam or composite resin type, is of the correct shape (i.e., ensuring proper contact between the cavity-containing tooth T and its neighbors), a pair of matrix band retainers R are employed to hold the matrix bands M in place and apply pressure thereto.

The resilience of matrix band retainers R urge the matrix bands M into the proper shape at the interproximal area to ensure that the adjacent teeth will maintain proper contact with one another after the filling has hardened. To aid in the separation and approximate the gingival portion of the tooth during the dental restoration process, a wedge W is placed in each interproximal area, as shown.

In the typical matrix system shown in FIG. 2, each matrix M is typically formed from a relatively thick metal sheet, and the wedge W is commonly formed from an absorbent material, such as wood. Combined with the matrix retainers R, the overall system is bulky, may irritate or injure the gingiva, and may result in either over-contoured or under-contoured walls of the tooth T. Additionally, the required separate matrix retainers R reduce the field of access in the patient's mouth and are typically uncomfortable for the patient. The interproximal wedge W is further cumbersome, particularly when used in between teeth with tight contact. Such wedges are also known to displace the gingival papilla, resulting in pain, irritation and gingival bleeding. Thus, an integral restoration matrix system solving the aforementioned problems is desired.

SUMMARY

The integral restoration matrix system provides a single tool for dental restorations, thereby obviating the need for a separate matrix band, interproximal wedge, and matrix retainer. The integral restoration matrix system includes an arcuate frame having an upper arcuate support member, at least one lower support member, and first and second opposed side support members. The arcuate frame includes an open interior region extending between the support members. A matrix sheet is secured to the arcuate frame and extends across, and covers, the open interior region defined by the arcuate frame. First and second upper arcuate retaining arms can be secured to, and extend from, respective upper ends of the first and second opposed side members. First and second lower arcuate retaining arms can be secured to, and extend from, respective lower ends of the first and second opposed side members. A hemostatic mesh can secured to the lower arcuate member of the arcuate frame. first and second secondary retaining arms may be secured to the lower arcuate member of the arcuate frame. In an alternative embodiment, at least one of the upper and lower sets of arcuate retaining arms can be replaced by elastic bands.

In use, the integral restoration matrix system can retain any excess moldable material, maintain the gingival papilla in place, control gingival fluids, and provide adequate isolation for bonding resin-based restoration.

These and other features of the present invention will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
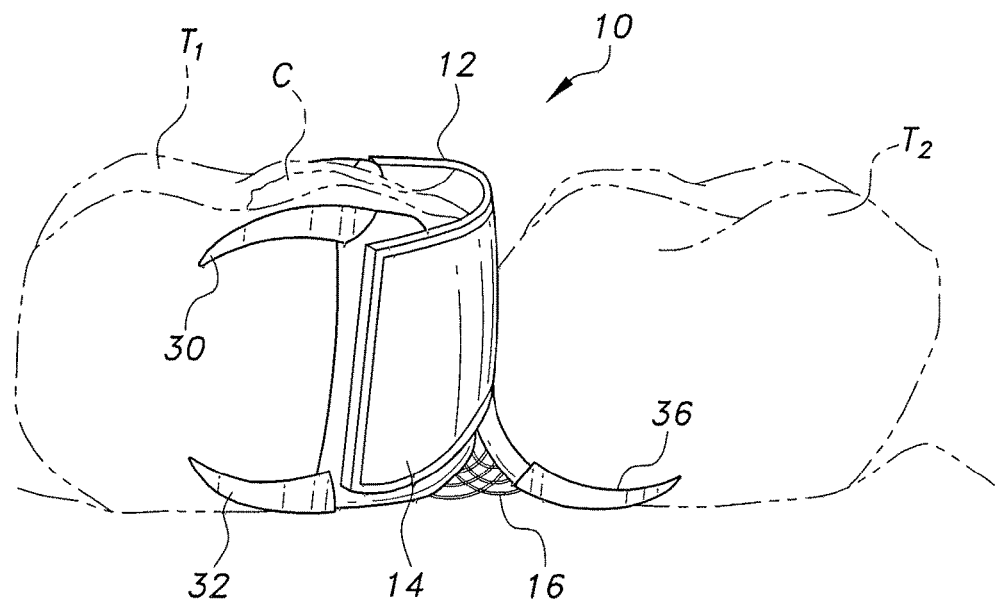
FIG. 1 is an environmental perspective view of an integral restoration matrix system.
Figure 2:
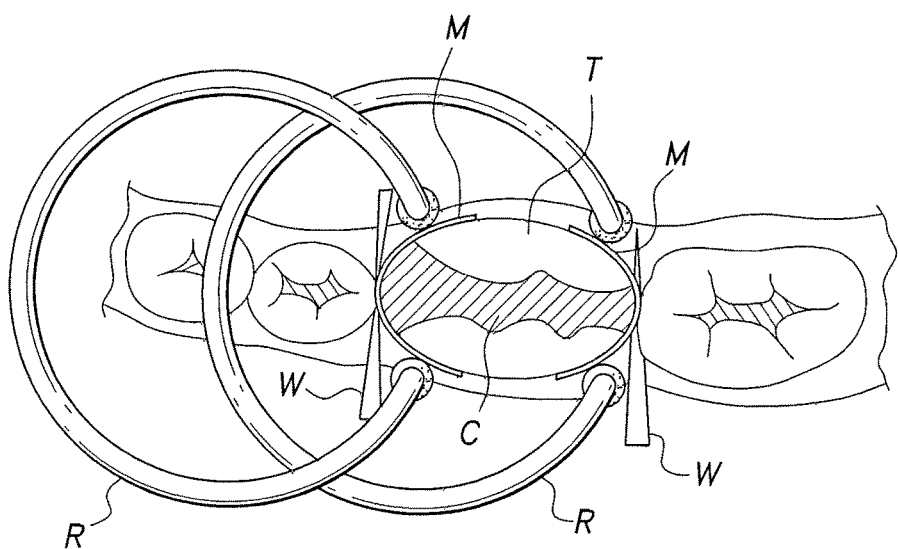
FIG. 2 is a top environmental view of a conventional prior art dental restoration matrix system.
Figure 3:
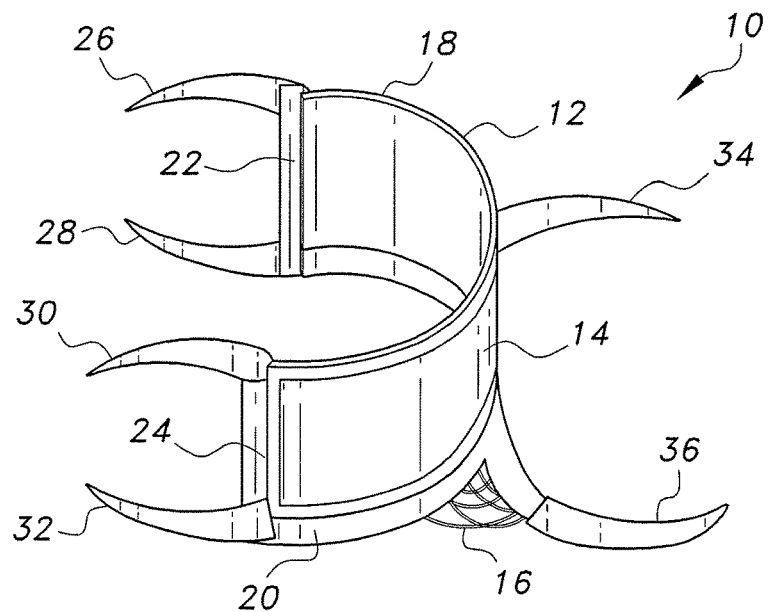
FIG. 3 is a perspective view of the integral restoration matrix system with first and second secondary retaining arms thereof being shown in a deployed state.
Figure 4:
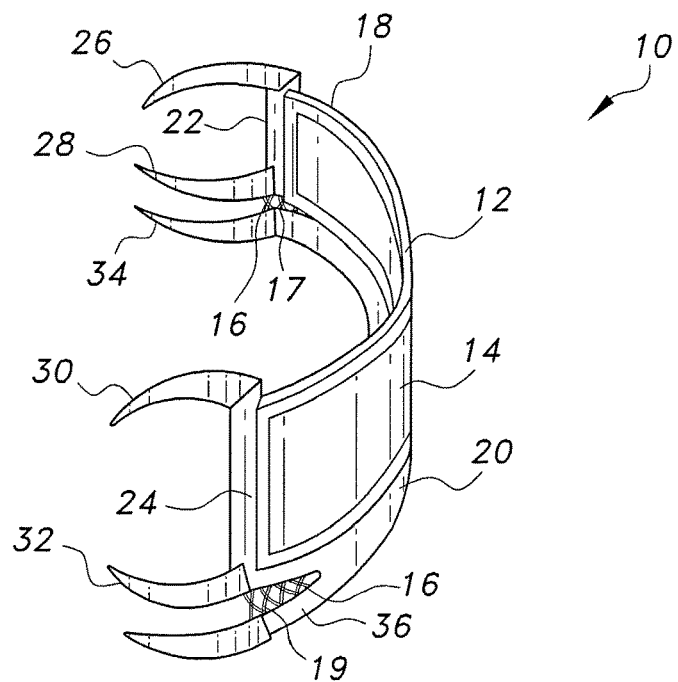
FIG. 4 is a perspective view of the integral restoration matrix system with the first and second secondary retaining arms being shown in a collapsed state.
Figure 5:
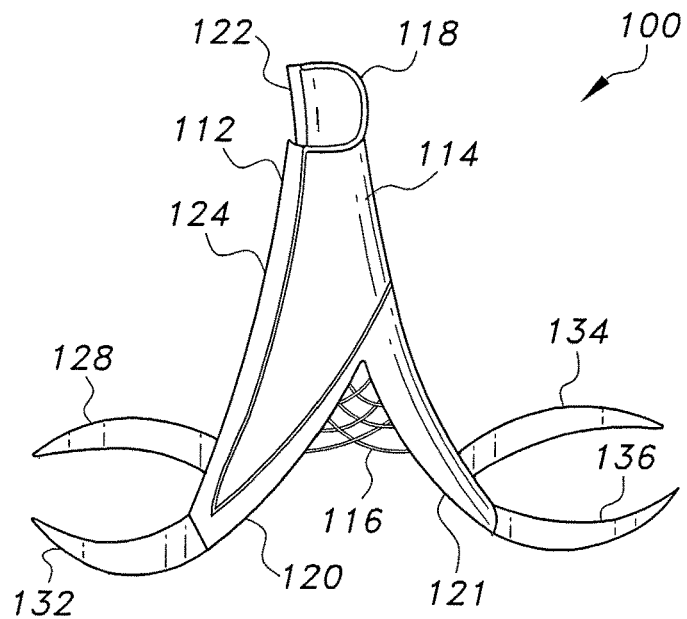
FIG. 5 is a perspective view of an alternative embodiment of the integral restoration matrix system.
Figure 6:
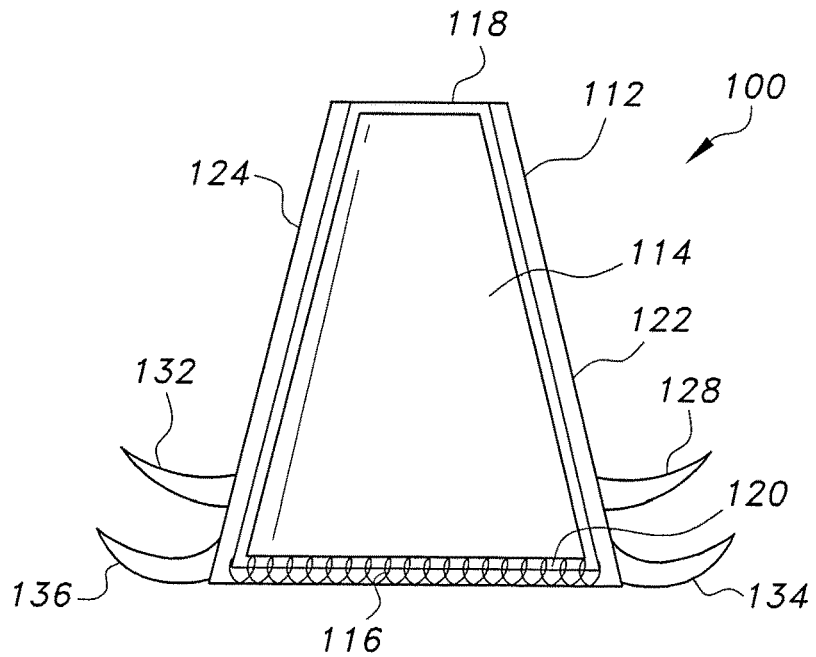
FIG. 6 is a front view of one side of the integral restoration matrix system of FIG. 5.

As shown in FIGS. 1, 3 and 4, an embodiment of the integral restoration matrix system 10 includes an arcuate frame 12 having an upper arcuate support member 18, at least one lower support member 20, and first and second opposed side support members 22, 24, respectively. The frame 12 may be formed from any suitable type of non-corrosive and non-toxic material, such as thin aluminum, a thin titanium alloy or the like. The arcuate frame 12 defines an open interior region, with a matrix sheet 14 being secured to arcuate frame 12 and extending across, and covering, the open interior region thereof. The matrix sheet 14, similar to a conventional dental restoration matrix, retains the moldable material used to fill cavity C in tooth $T_1$ (as shown in FIG. 1). The matrix sheet 14 may be made of any suitable type of material, such as, for example, a stretchable double sheet of plastic or the like. For such a double sheet used for conventional dental restoration, each layer of sheet 14 may have a thickness on the order of about 0.01 mm. Typically, the moldable material used to fill cavity C in tooth $T_1$ would have a thickness on the order of about 0.05-0.2 mm.

First and second upper arcuate retaining arms 26, 30, respectively, can be secured to, and extend from, respective upper ends of the first and second opposed side members 22, 24, respectively. Similarly, first and second lower arcuate retaining arms 28, 32, respectively, can be secured to, and extend from, respective lower ends of the first and second opposed side members 22, 24, respectively. A hemostatic mesh 16 can be secured to the lower arcuate member 20 of the arcuate frame 12. The retaining arms 26, 30, 28, 32 may be formed from any suitable type of non-corrosive and non-toxic material, such as aluminum, stainless steel or the like. The hemostatic mesh 16 may be any suitable type of mesh formed from a hemostatic material or mesh coated with a hemostatic agent.

In use, the first and second upper arcuate retaining arms 26, 30 are adapted for releasably grasping a coronal portion of a tooth to be restored (tooth $T_1$ in FIG. 1), and the first and second lower arcuate retaining arms 28, 32 are adapted for releasably grasping a cervical portion of tooth $T_1$. The hemostatic mesh 16 is adapted for positioning against an adjacent gingival papilla and acts in a manner similar to a conventional interproximal wedge in a conventional matrix system. Any excess moldable material used to fill cavity C in tooth $T_1$ may flow gingivally and be retained by the hemostatic mesh 16. In addition to retaining any excess moldable material, the hemostatic mesh 16 maintains the gingival papilla in place, controls gingival fluids, and provides adequate isolation for bonding resin-based based restoration.

Additionally, first and second secondary retaining arms 34, 36, respectively, may extend from the lower arcuate member 20 of the arcuate frame 12. In use, the first and second secondary retaining arms 34, 36 are adapted for releasably grasping a gingival portion of a tooth adjacent the tooth being restored (tooth $T_2$ in FIG. 1). Preferably, the first and second secondary retaining arms 34, 36 are selectively collapsible, allowing them to extend rearwardly and be positioned against the first and second lower arcuate retaining arms 28, 32 when not in use (as shown in FIG. 4), and to be extended forwardly, toward the adjacent tooth $T_2$, when in use (as shown in FIGS. 1 and 3). As shown in FIG. 4, a first portion 17 of the hemostatic mesh 16 extends between the first secondary retaining arm 34 and the first lower arcuate retaining arm 28, and a second portion 19 of the hemostatic mesh 16 extends between the second secondary retaining arm 36 and the second lower arcuate retaining arm 32. In use, first and second secondary retaining arms 34, 36 may be used to adjust the width of the restored cavity C in relation to the adjacent tooth $T_2$. Additionally, first and second secondary retaining arms 34, 36 can serve to retain the matrix sheet 14 in place.

Figure 7:
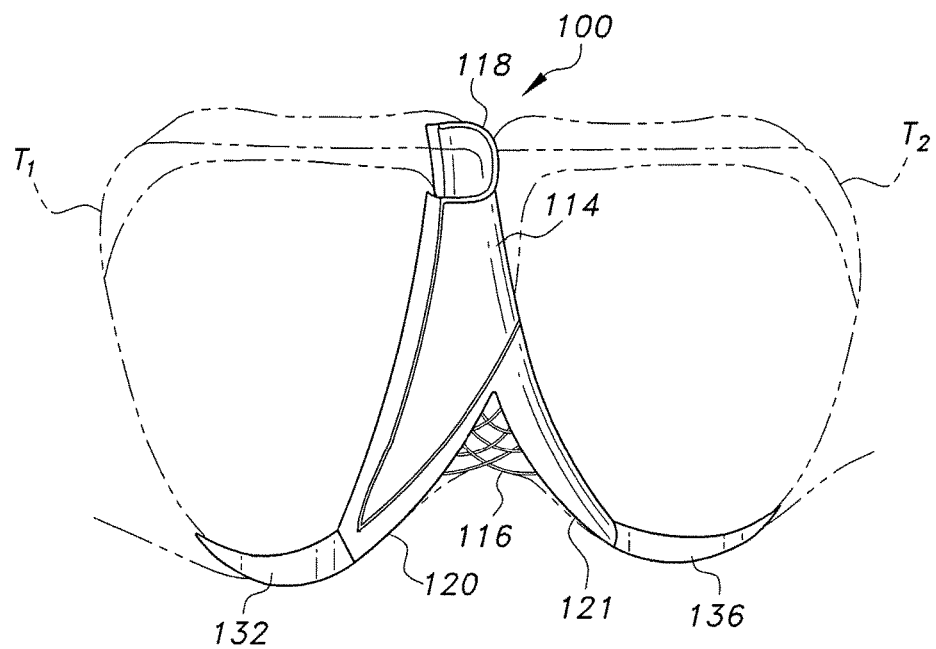
FIG. 7 is an environmental perspective view of the integral restoration matrix system of FIG. 5.

FIGS. 5-8 depict an alternative embodiment of the integral restoration matrix system. The embodiment depicted in FIGS. 5-8 can be particularly useful for restoring interproximal cavities in anterior teeth. The integral restoration matrix 100 is similar to integral restoration matrix system 10 except that the integral restoration matrix 100 does not include the first and second upper arcuate retaining arms. Further, frame 112 of the integral restoration matrix system 100 has a generally inverted V shape and includes an arcuate top support member 118, a first bottom member 120, and a second bottom member 121. The first bottom member 120 and the second bottom member 121 join together to form a generally inverted V configuration. Like the previous embodiment, the frame 112 includes first and second opposed side members 122, 124, and an open interior region between the side members 122, 124*a*. The first bottom member 120 extends toward and connects with the side members 122, 124. The second bottom member 121 extends in a direction away from the side members 122, 124. A matrix sheet 114 is secured to the frame 112 and extends across, and covers, the open interior region defined by the frame 112. First and second lower arcuate retaining arms 128, 132, respectively, are secured to, and extend from, respective lower ends of the first and second opposed side members 122, 124. A hemostatic mesh 116 extends between the first bottom member 120 and the second bottom member 121. In use, the first and second lower arcuate retaining arms 128, 132 are adapted for releasably grasping a cervical portion of the tooth to be restored (tooth $T_1$ in FIG. 7), and the hemostatic mesh 116 is adapted for positioning against an adjacent gingival papilla. First and second secondary retaining arms 134, 136 may be secured to the second bottom member 121. In use, as shown in FIG. 7, the first and second secondary retaining arms 134, 136 are adapted for releasably grasping a gingival portion of a tooth adjacent the tooth being restored (tooth $T_2$ in FIG. 7).

Figure 8:
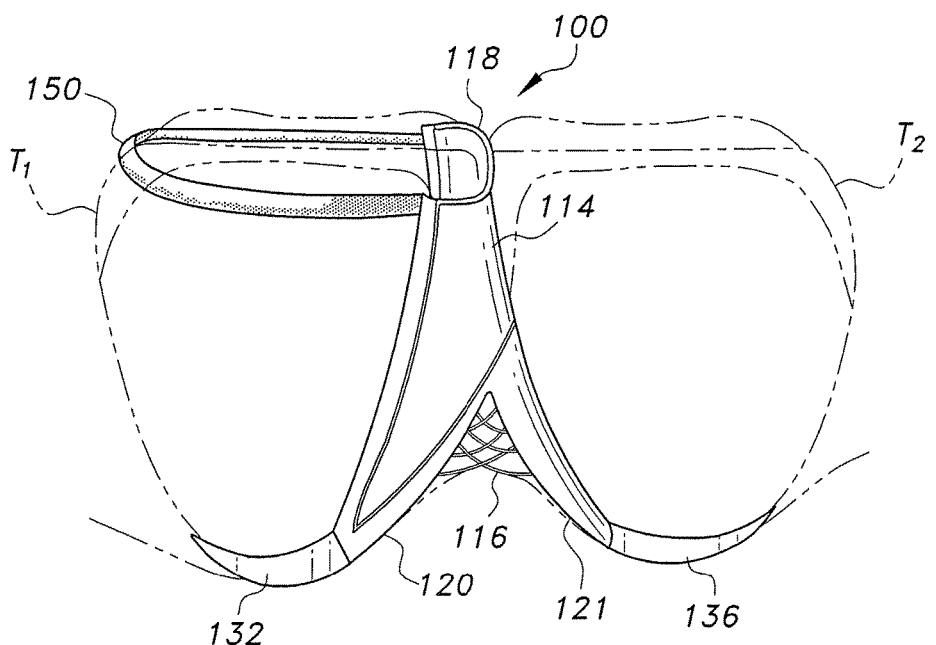
FIG. 8 is an environmental perspective view of a further alternative embodiment of the integral restoration matrix system.

Preferably, as in the previous embodiment, the first and second secondary retaining arms 134, 136 are selectively collapsible, allowing them to extend rearwardly and be positioned against the first and second lower arcuate retaining arms 128, 132 when not in use, and to be extended forwardly, toward the adjacent tooth $T_2$, when in use. The second bottom member 121 can also be foldable or collapsible. As in the previous embodiment, a first portion of the hemostatic mesh 116 preferably extends between the first secondary retaining arm 134 and the first lower arcuate retaining arm 128, and a second portion of the hemostatic mesh 116 preferably extends between the second secondary retaining arm 136 and the second lower arcuate retaining arm 132. As shown in FIG. 8, rather than the first and second upper arcuate retaining arms 26, 30 of the previous embodiment, an elastic band 150 may be secured to respective upper ends of the first and second opposed side members 122, 124. In use, the elastic band 150 is adapted for releasably grasping a coronal portion of tooth $T_1$, as shown. Elastic band 150 may have a thickness on the order of about 0.05-0.2 mm.

Figure 9:
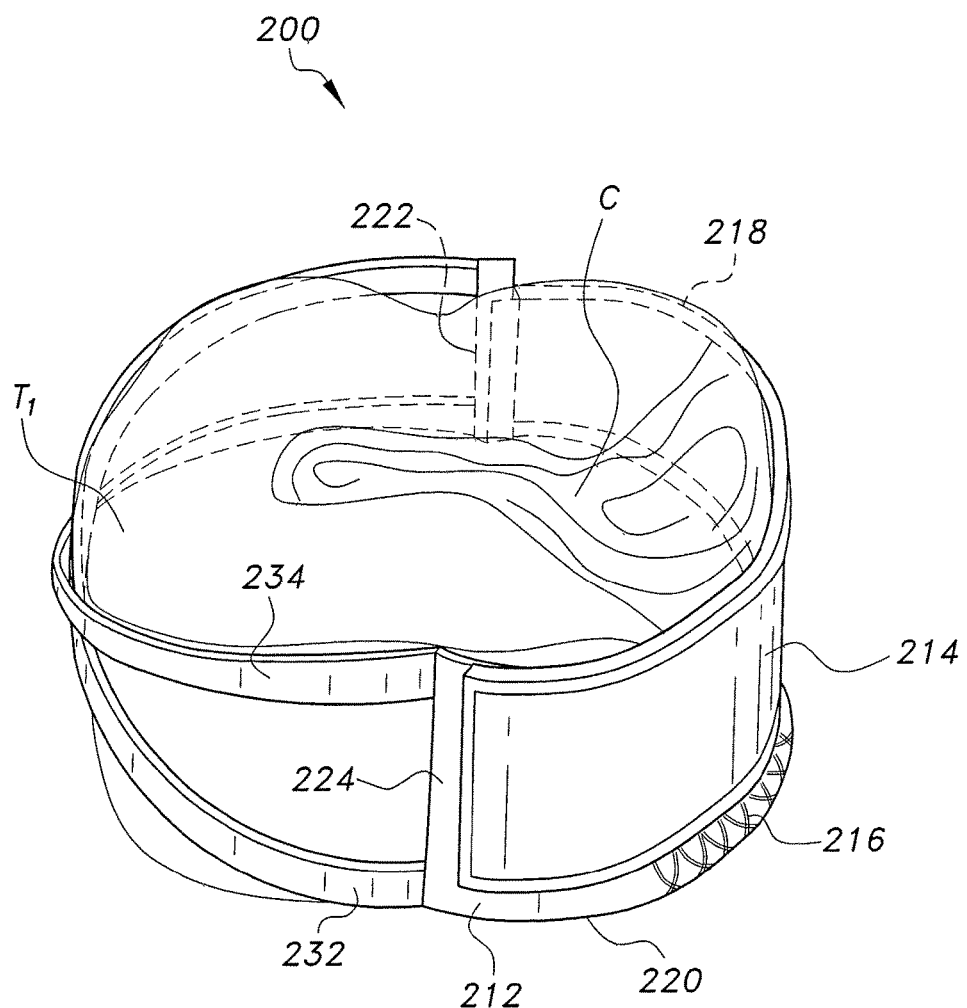
FIG. 9 is an environmental perspective view of still another alternative embodiment of the integral restoration matrix system.

The alternative embodiment depicted in FIG. 9 is similar to the embodiment depicted in FIGS. 1, 3, and 4, except that, the upper and lower sets of arcuate retaining arms of FIGS. 1, 3 and 4 are replaced by first and second elastic bands 232, 234. Similar to the embodiments of FIGS. 1, 3, and 4, the integral restoration matrix system 200 of FIG. 9 includes an arcuate frame 212 having opposed upper and lower arcuate members 218, 220, respectively, and first and second opposed side members 222, 224, respectively, with the arcuate frame 212 defining an open interior region. A matrix sheet 214 is secured to the arcuate frame 212 and extends across, and covers, the open interior region defined by the arcuate frame 212. One end of the first elastic band 232 is secured to an upper end of the first side member 222, and an opposed end of the first elastic band 232 is secured to a lower end of the second side member 224, as shown. A second elastic band 234 crisscrosses over the first elastic band 232, with one end of the second elastic band 234 being secured to a lower end of the first side member 222, and an opposed end of the second elastic band 234 is secured to an upper end of the second side member 224. First and second elastic bands 232, 234 may each have a thickness on the order of about 0.05-0.2 mm.

A hemostatic mesh 216 is secured to the lower arcuate member 220 of the arcuate frame 212. In use, the first and second elastic bands 232, 234 are adapted for releasably grasping coronal and cervical portions of the tooth to be restored (tooth $T_1$ in FIG. 9), and the hemostatic mesh 216 is adapted for positioning against an adjacent gingival papilla.

It is to be understood that the integral restoration matrix system is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. An integral restoration matrix system, comprising:
   a frame having an arcuate upper support member, at least one lower support member spaced from the upper support member and first and second opposed side support members, the arcuate upper support member defining an open interior region;
   a matrix sheet secured to the arcuate frame, the matrix sheet extending across and covering the open interior region defined by the arcuate frame; and
   a hemostatic mesh secured to the at least one lower member of the arcuate frame, the hemostatic mesh being adapted for positioning against a gingival papilla.

2. The integral restoration matrix system as recited in claim 1, further comprising:
   a first elastic band having a first set of opposed ends, one of the first set of opposed ends being secured to an upper end of the first side member, another one of the first set of opposed ends being secured to a lower end of the second side member; and
   a second elastic band having a second set of opposed ends, one of the second set of opposed ends being secured to an upper end of the second side member, another one of the second set of opposed ends being secured to a lower end of the first side member.

3. The integral restoration matrix system as recited in claim 1, further comprising first and second upper arcuate retaining arms secured to, and extending from, respective upper ends of the first and second opposed side support members, whereby the first and second upper arcuate retaining arms are adapted for releasably grasping a coronal portion of a tooth to be restored.

4. The integral restoration matrix system as recited in claim 1, further comprising first and second lower arcuate retaining arms secured to, and extending from, respective lower ends of the first and second opposed side support members, whereby the first and second lower arcuate retaining arms are adapted for releasably grasping a cervical portion of the tooth to be restored.

5. The integral restoration matrix system as recited in claim 4, further comprising first and second secondary retaining arms secured to the at least one lower member of the frame, whereby the first and second secondary retaining arms are adapted for releasably grasping a gingival portion of an adjacent tooth.

6. The integral restoration matrix system as recited in claim 5, wherein the first and second secondary retaining arms are selectively collapsible and a first portion of the hemostatic mesh extends between the first secondary retaining arm and the first lower arcuate retaining arm, and a second portion of the hemostatic mesh extends between the second secondary retaining arm and the second lower arcuate retaining arm.

7. The integral restoration matrix system as recited in claim 4, wherein:
   the at least one lower member comprises a first lower member and a second lower member, the first lower member and the second lower member together forming a generally inverted V-shaped configuration;
   the second lower member is attached to first and second secondary retaining arms, the first and second secondary retaining arms being selectively collapsible;
   and a first portion of the hemostatic mesh extends between the first secondary retaining arm and the first lower arcuate retaining arm, and a second portion of the hemostatic mesh extends between the second secondary retaining arm and the second lower arcuate retaining arm.

8. The integral restoration matrix system as recited in claim 7, further comprising an elastic band secured to respective upper ends of the first and second opposed side members, whereby the elastic band is adapted for releasably grasping a coronal portion of the tooth to be restored.

9. The integral restoration matrix system as recited in claim 1, further comprising:
   a first elastic band having opposed ends, one of the opposed ends being secured to an upper end of the first side member, another one of the opposed ends being secured to a lower end of the second side member; and
   a second elastic band having opposed ends, one of the opposed ends being secured to an upper end of the second side member, another one of the opposed ends being secured to a lower end of the first side member,
   whereby the first and second elastic bands are adapted for releasably grasping coronal and cervical portions of a tooth to be restored, and the hemostatic mesh is adapted for positioning against an adjacent gingival papilla.

10. An integral restoration matrix system, comprising:
    an arcuate frame having opposed upper and lower arcuate members and first and second opposed side members, the arcuate frame defining an open interior region;
    a matrix sheet secured to the arcuate frame, the matrix sheet extending across and covering the open interior region defined by the arcuate frame;
    first and second upper arcuate retaining arms secured to, and extending from, respective upper ends of the first and second opposed side members, the first and second upper arcuate retaining arms being selectively collapsible;
    first and second lower arcuate retaining arms secured to, and extending from, respective lower ends of the first and second opposed side members, the first and second lower arcuate retaining arms being selectively collapsible; and
    a hemostatic mesh secured to the lower arcuate member of the arcuate frame,
    whereby the first and second upper arcuate retaining arms are adapted for releasably grasping a coronal portion of a tooth to be restored, the first and second lower arcuate retaining arms are adapted for releasably grasping a cervical portion of the tooth to be restored, and the hemostatic mesh is adapted for positioning against an adjacent gingival papilla.

11. The integral restoration matrix system as recited in claim 10, further comprising first and second secondary retaining arms secured to the lower arcuate member of the arcuate frame, whereby the first and second secondary retaining arms are adapted for releasably grasping a gingival portion of an adjacent tooth.

12. The integral restoration matrix system as recited in claim 11, wherein a first portion of the hemostatic mesh extends between the first secondary retaining arm and the first lower arcuate retaining arm, and a second portion of the hemostatic mesh extends between the second secondary retaining arm and the second lower arcuate retaining arm.

13. An integral restoration matrix system, comprising:
  an arcuate frame having opposed upper and lower arcuate members and first and second opposed side members, the arcuate frame defining an open interior region;
  a matrix sheet secured to the arcuate frame, the matrix sheet extending across and covering the open interior region defined by the arcuate frame;
  a first elastic band having opposed ends, one of the opposed ends being secured to an upper end of the first side member, another one of the opposed ends being secured to a lower end of the second side member;
  a second elastic band having opposed ends, one of the opposed ends being secured to an upper end of the second side member, another one of the opposed ends being secured to a lower end of the first side member; and
  a hemostatic mesh secured to the lower arcuate member of the arcuate frame,
  whereby the first and second elastic bands are adapted for releasably grasping coronal and cervical portions of a tooth to be restored, and the hemostatic mesh is adapted for positioning against an adjacent gingival papilla.

* * * * *